United States Patent
Okawa et al.

(10) Patent No.: US 7,030,259 B2
(45) Date of Patent: Apr. 18, 2006

(54) PROCESS FOR THE PREPARATION OF SILICONE COMPOUNDS

(75) Inventors: Tadashi Okawa, Chiba (JP); Makoto Yoshitake, Chiba (JP); Tomohiro Iimura, Chiba (JP); Satoshi Onodera, Chiba (JP)

(73) Assignee: Dow Corning Toray Silicone Co., Ltd., (JP)

( * ) Notice: Subject to any disclaimer, the term of this patent is extended or adjusted under 35 U.S.C. 154(b) by 35 days.

(21) Appl. No.: 10/519,636

(22) PCT Filed: Jan. 27, 2003

(86) PCT No.: PCT/JP03/00746

§ 371 (c)(1),
(2), (4) Date: Aug. 11, 2004

(87) PCT Pub. No.: WO03/064436

PCT Pub. Date: Aug. 7, 2003

(65) Prior Publication Data

US 2005/0256330 A1    Nov. 17, 2005

(30) Foreign Application Priority Data

Jan. 31, 2002    (JP) ............................. 2002-024434

(51) Int. Cl.
*C07C 7/04*    (2006.01)

(52) U.S. Cl. ..................................................... 556/451
(58) Field of Classification Search ................ 556/450, 556/451
See application file for complete search history.

(56) References Cited

U.S. PATENT DOCUMENTS 6,147,243 A * 11/2000 Onodera et al. ............ 556/451

FOREIGN PATENT DOCUMENTS

| JP | HEI 11-217389 | 8/1999 |
| JP | 2000-186095 | 7/2000 |

\* cited by examiner

*Primary Examiner*—J. Parsa
(74) *Attorney, Agent, or Firm*—Robert L. McKellar; McKellar IP Law, PLLC

(57) ABSTRACT

A process for preparing a silicone compound, the process comprising reacting (A) a silicon compound having silicon-bonded alkoxy groups or silicon-bonded aryloxy groups and (B) a disiloxane in the presence of (C) a carboxylic acid, (D) an acid catalyst, and (E) a carboxylic anhydride, and a process for preparing a silicone compound, the process comprising reacting (F) a silicon compound having silicon-bonded acyloxy groups and (B) a disiloxane compound in the presence of (D) an acid catalyst, (E) a carboxylic anhydride, and (G) an alcohol.

12 Claims, No Drawings

PROCESS FOR THE PREPARATION OF SILICONE COMPOUNDS

The present invention relates to processes used for the preparation of silicone compounds, and, more particularly, to processes for the high-yield preparation of high-purity silicone compounds formed by the substitution of siloxy groups for silicon-bonded alkoxy, aryloxy, or acyloxy groups in silicon compounds.

Presently known processes used for substituting siloxy groups for silicon-bonded alkoxy, aryloxy, or acyloxy groups in silicon compounds include, for instance, processes for the preparation of 3-methacryloxypropyltris(trimethylsiloxy)silane by reacting hexamethyldisiloxane with 3-methacryloxypropyltrimethoxysilane in the presence of acetic acid and an acid catalyst (see Japanese Patent Application Publication(Kokai) No. Hei 11-217389 and Japanese Patent Application Publication(Kokai) No. 2000-186095).

However, in the process proposed in Japanese Patent Application Publication(Kokai) No. Hei 11-217389, acetic acid reacts with methanol produced in the reaction system to form water and methyl acetate as by-products. The disadvantage of the process is that the water formed as a by-product causes separation of the reaction system into an oil layer and a water layer, thereby increasing the time required to bring the reaction to completion, and that alkoxy, aryloxy, and acyloxy groups involved in the reaction undergo direct hydrolysis and produce silanol groups, as a result of which the purity of the target substance decreases. Another disadvantage is the high polarity of the other simultaneously formed by-product, methyl acetate, as a result of which washing operations performed upon termination of the reaction in order to remove the acid catalyst and acetic acid result in the migration of the target substance to the water phase following dissolution of methyl acetate in water, which reduces the yield.

On the other hand, the disadvantages of the process proposed in Japanese Patent Application Publication(Kokai) No. 2000-186095 include a long reaction time and low productivity due to the low temperatures at which the reaction is carried out.

The present invention is a result of in-depth investigations aimed at resolving the above-described problems.

Namely, it is an object of the present invention to provide processes for the high-yield preparation of high-purity silicone compounds formed by the substitution of siloxy groups for silicon-bonded alkoxy, aryloxy, or acyloxy groups in silicon compounds.

The present invention relates to a first process for preparing a silicone compound, the process comprising reacting (A) a silicon compound having silicon-bonded alkoxy groups or silicon-bonded aryloxy groups and (B) a disiloxane compound having the formula:

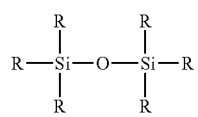

wherein R is an unsubstituted or substituted monovalent hydrocarbon group or a hydrogen atom, in the presence of (C) a carboxylic acid, (D) an acid catalyst, and (E) a carboxylic anhydride. The silicone compound is formed by substitution of siloxy groups of component (B) for some or all of the silicon-bonded alkoxy or aryloxy groups of component (A).

In addition, the present invention relates to a second process for preparing a silicone compound, the process comprising reacting (F) a silicon compound having silicon-bonded acyloxy groups and (B) a disiloxane compound having the formula:

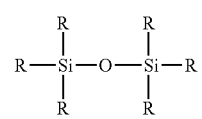

wherein R is an unsubstituted or substituted monovalent hydrocarbon group or a hydrogen atom, in the presence of (D) an acid catalyst, (E) a carboxylic anhydride, and (G) an alcohol. The silicone compound is formed by substitution of siloxy groups of component (B) for some or all of the silicon-bonded acyloxy groups of component (F).

First of all, detailed explanations are provided regarding the first of the above-mentioned processes used for the preparation of silicone compounds. The silicon-bonded alkoxy groups of component (A) are exemplified by methoxy, ethoxy, propoxy, and butoxy groups, and the aryloxy groups are exemplified by phenoxy groups. Although there are no limitations concerning the molecular weight of component (A), preferably, it should not be higher than 100,000 because there is a marked drop in reactivity and the rate of conversion to the target silicone compounds tends to exhibit a marked decrease when it exceeds 100,000. In the preparation process of the present invention, component (A) is preferably a compound having silicon-bonded alkoxy groups, with methoxy or ethoxy groups being particularly preferable as the alkoxy groups because of their excellent reactivity.

Component (A) is exemplified by tetramethoxysilane, tetraethoxysilane, and other tetraalkoxysilane compounds; trimethoxysilane, triethoxysilane, methyltrimethoxysilane, methyltriethoxysilane, vinyltrimethoxysilane, allyltrimethoxysilane, phenyltrimethoxysilane, propyltrimethoxysilane, 3-methacryloxypropyltrimethoxysilane, 3-acryloxypropyltrimethoxysilane, 3-chloropropyltrimethoxysilane, 3-trifluoropropyltrimethoxysilane, 3-mercaptopropyltrimethoxysilane, bis(trimethoxypropyl)disulfide silane, bis(trimethoxypropyl)tetrasulfide silane, bis(triethoxypropyl)disulfide silane, bis(triethoxypropyl)tetrasulfide silane, and other trialkoxysilane compounds; dimethyldimethoxysilane, dimethyldiethoxysilane, vinylimethyldimethoxysilane, phenylmethyldimethoxysilane, 3-methacryloxypropylmethyldimethoxysilane, 3-mercaptopropylmethyldimethoxysilane, and other dialkoxysilane compounds; monoalkoxysilane compounds, such as trimethylmethoxysilane, trimethylethoxysilane, phenyldimethylmethoxysilane, 3-methacryloxypropyldimethylmethoxysilane, 3-mercaptopropyldimethylmethoxysilane, and vinyldimethylinethoxysilane, as well as other alkoxysilane compounds; partial condensation products of such alkoxysilane compounds; 1-methoxy-1,1,3,3,5,5,7,7-octamethyltetrasiloxane, 1-methoxy-nonamethyltetrasiloxane, 1-methoxy-7-vinyl-octamethyltetrasiloxane, and other alkoxy-containing siloxane compounds.

Component (B) is a disiloxane compound represented by the general formula:

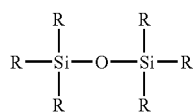

where R stands for an unsubstituted or substituted monovalent hydrocarbon group or a hydrogen atom. The monovalent hydrocarbon groups are exemplified by methyl, ethyl, propyl, and other alkyl groups; vinyl, allyl, butenyl, hexenyl, octenyl, and other alkenyl groups; phenyl, tolyl, xylyl, and other aryl groups; benzyl, phenetyl, and other aralkyl groups; 3-methacryloxypropyl, 3-acryloxypropyl, 3-mercaptopropyl, 3-chloropropyl, 3-bromopropyl, 3,3,3-trifluoropropyl, and other substituted alkyl groups. Additionally, while the R groups in a molecule may be identical or different, it is preferred that there should be one hydrogen atom per silicon atom. Component (B) is exemplified by 1,1,3,3-tetramethyldisiloxane, hexamethyldisiloxane, 1,3-dipropyltetramethyldisiloxane, 1,3-divinyltetramethyldisiloxane, 1,3-diphenyltetramethyldisiloxane, and 1,3-bis(3-methacryloxypropyl)tetramethyldisiloxane.

Although there are no limitations concerning the mole ratio of component (B) to component (A), to substitute siloxy groups for all the silicon-bonded alkoxy or aryloxy groups in component (A), it is preferable to add not less than 0.5 mol of component (B) per 1 mol of the alkoxy or aryloxy groups of component (A). In practical terms, the mole ratio is preferably in the range of from 0.5 to 1, and, especially, in the range of from 0.5 to 0.75.

The carboxylic acid of (C) is essential for carrying out the reaction, and although the mechanism of its action is unclear, it is believed that the acid promotes the reaction of silylation of component (A) in the reaction of component (A) and component (B), which is an equilibrium reaction. In order to fully silylate the silicon-bonded alkoxy or aryloxy groups in component (A), it is preferable to use about 0.5 to 10 mol of component (C) per 1 mol of the alkoxy or aryloxy groups of component (A). Component (C) is exemplified by aliphatic carboxylic acids such as formic acid, acetic acid, propionic acid, and maleic acid, as well as by aromatic carboxylic acids such as benzoic acid and substituted benzoic acids. Among them, formic acid and acetic acid are preferrable as acids that sufficiently promote the silylation reaction.

The acid catalyst of (D) is used to promote the above-described reaction. Component (D) is exemplified by hydrochloric acid, sulfuric acid, trifluoroacetic acid, trifluoromethanesulfonic acid, and other protonic acids; iron chloride, aluminum chloride, zinc chloride, titanium chloride, and other Lewis acids. In the present invention, it is preferable to use strong acids in order to improve the conversion rate of the reaction. Specifically, hydrochloric acid, sulfuric acid, and perfluoroalkanesulfonic acids are preferred, with trifluoromethanesulfonic acid being especially preferable. When a strong acid is used as component (D), it is preferable to add just a trace amount of the strong acid sufficient to bring about the silylation reaction in order to suppress side reactions such as reactions involving random rearrangement of siloxane bonds in the target silicone compounds, homocondensation of the silicon-bonded alkoxy groups or aryloxy groups, etc. Although its amount depends on the acid strength of the acid catalyst used and other parameters and thus cannot be given for all possible cases, an amount of about 10 to 10,000 ppm based on the total amount of the reaction mixture is sufficient in case of trifluoromethanesulfonic acid. In addition, the smaller the amount of the acid used, the greater the reduction in the amount of the basic compounds used for its neutralization and the amount of water used for washing it out. From this point of view, it is also preferable to use the acid catalyst in the smallest amount necessary.

The carboxylic anhydride of (E), which constitutes a characteristic feature of the present invention, has the function of capturing the alcohol or water formed as by-products in the reaction of the above-described components (A) through (D). As a result, the reaction system does not separate into two layers and the reaction proceeds quickly; at the same time, the amount of silanol groups etc. formed as by-products decreases and the target silicone compounds are obtained in high yield. Component (E) is exemplified by anhydrides of aliphatic carboxylic acids such as acetic anhydride, propionic anhydride, maleic anhydride, etc., as well as by anhydrides of aromatic carboxylic acids such as benzoic anhydride and the like. Among them, acetic anhydride and propionic anhydride are preferable because they sufficiently promote the above-mentioned reaction. The amount, in which component (E) is added, is preferably about 0.5 to 1.0 mol per 1 mol of component (C). In addition, although there are no particular limitations concerning the order, in which component (E) is added, it is preferable to add it after component (A) and component (B) have been reacted to some extent in the presence of component (C) and component (D).

The first preparation process of the present invention is characterized by substituting the siloxy groups of component (B) for the silicon-bonded alkoxy or aryloxy groups of component (A) by reacting component (A) and component (B) in the presence of component (C), component (D), and component (E). Although the reaction can be conducted without a solvent, the rate of the reaction can be regulated by diluting the reaction system with an organic solvent that does not directly participate in the reaction. Organic solvents used in such a case are exemplified by hexane, heptane, acetone, methyl ethyl ketone, benzene, toluene, and xylene.

Although there are no limitations concerning the order of operations in the first preparation process of the present invention, for excellent reaction heat control, productivity, and reaction selectivity, it is preferable to use a process in which, after mixing component (B), component (C), and component (D), component (A) is added while heating or cooling the system as needed, and component (E) is further added upon lapse of 30 min to several hours. In the preparation process of the present invention, the progress of the reaction is tracked by gas chromatography etc., and, upon confirmation that a state of equilibrium has been achieved to a substantial degree, the acid is neutralized with a base. Furthermore, if necessary, the target silicone compounds can be obtained by removing the acids and salts from the reaction system by washing etc. and using distillation and other conventional well-known methods. Organic amines, ammonia, hexamethyldisilazane, and other nitrogen-containing compounds, inorganic substances, such as calcium carbonate, etc., are suggested as bases used in the neutralization reaction. Although the temperature of the reaction varies depending on the combination of component (A) and component (B) and cannot be given for all possible cases, in general, it is preferred that the temperature should be in the range of from 0 to 80° C., and, especially, in the range of from 20 to 70° C. This is due to the tendency of the reaction to slow down when the reaction temperature is below the above range, and, on the other hand, to the homocondensation of component (A) and the reaction of random rearrangement of siloxane bonds in the resultant silicone compounds when it exceeds the range. In particular, when component (A) and component (B) have silicon-bonded hydrogen atoms, the reaction is preferably conducted at a temperature of from 0 to 80° C. because otherwise there is a tendency to bring about side reactions such as the dehydration condensation with hydroxyl groups contained in the reaction system.

Next, detailed explanations are provided regarding the second of the above-mentioned processes. The silicon-bonded acyloxy groups in silicon compound (F) are exemplified by acetoxy, propionyloxy, and benzoyloxy, with acetoxy being preferable. Although there are no limitations concerning the molecular weight of component ( F), it should preferably be not higher than 100,000 because there is a marked drop in reactivity and the rate of conversion to the target silicone compounds tends to exhibit a marked decrease when it exceeds 100,000.

Component (F) is exemplified by tetraacetoxysilane, and other tetraacyloxysilane compounds; triacetoxysilane, methyltriacetoxysilane, propyltriacetoxysilane, phenyltriacetoxysilane, vinyltriacetoxysilane, 3-chloropropyltriacetoxysilane, 3-mercaptopropyltriacetoxysilane, 3-methacryloxypropyltriacetoxysilane, and other triacyloxysilane compounds; dimethyldiacetoxysilane, 3-methacryloxypropylmethyldiacetoxysilane, and other diacyloxysilane compounds; monoacyloxysilane compounds, such as trimethylacetoxysilane and 3-methacryloxypropyldimethylacetoxysilane, as well as other acyloxysilane compounds; partial condensation products of such acyloxysilane compounds; 1-acetoxy-octamethyltetrasiloxane, 1-acetoxy-nonamethyltetrasiloxane, 1-acetoxy-7-vinyl-octamethyltetrasiloxane, and other acyloxy-containing siloxane compounds.

The disiloxane compound of (B) is the same as above. Although there are no limitations concerning the mole ratio of component (B) to component (F), to substitute siloxy groups for all the silicon-bonded acyloxy groups of component (F), it is preferable to add not less than 0.5 mol of component (B) per 1 mol of the acyloxy groups of component (F). In practical terms, the mole ratio is preferably in the range of from 0.5 to 1, and, especially, in the range of from 0.5 to 0.75.

The alcohol of (G), which is an essential component in the preparation process of the present invention, has the function of alkoxylating the silicon-bonded acyloxy groups of component (F). After the alkoxylation, the same silylation reaction takes place as in the process described above. Component (G) permits substitution of siloxy groups for silicon-bonded acyloxy groups in component (F) while maintaining the chemical structure of component (F) and makes it possible to obtain the target silicone compounds with high selectivity. Component (G) is exemplified by methanol, ethanol, isopropyl alcohol, phenol, and substituted phenols. Among them, methanol and ethanol are preferable due to their high reactivity. The amount, in which component (G) is added, is preferably not less than 0.5 mol per 1 mol of the silicon-bonded acyloxy groups of component (F). Furthermore, adding about 1 to 10 mol of component (G) per 1 mol of the silicon-bonded acyloxy groups of component (F) is even more preferable because this amount effectively promotes the reaction of silylation of component (F) in the equilibrium reaction of component (F) and component (B).

The acid catalyst of (D) is the same as above. When strong acids are used, it is preferable to add just a minimum amount sufficient to bring about the silylation reaction in order to suppress side reactions, such as reactions involving random rearrangement of siloxane bonds in the target silicone compounds, homocondensation of the silicon-bonded acyloxy groups, etc.

The carboxylic anhydride of (E), which constitutes a characteristic feature of the present invention, has the function of eliminating the alcohol and excess water formed as by-products during the reaction. The same anhydrides of aliphatic carboxylic acids and anhydrides of aromatic carboxylic acids as those mentioned above are suggested as component (E). Among them, acetic anhydride and propionic anhydride are preferred because they promote the reaction to a sufficient degree. The amount, in which component (E) is added, is preferably about 0.5 to 1.0 mol per 1 mol of component (G). In addition, although there are no particular limitations concerning the order in which component (E) is added, it is preferable to add it after component (F) and component (B) have been reacted to some extent in the presence of component (G) and component (D).

The second preparation process of the present invention is characterized by substituting the siloxy groups of component (B) for the silicon-bonded acyloxy groups of component (F) by reacting component (F) and component (B) in the presence of component (G), component (D), and component (E). Although the reaction can be conducted without a solvent, the rate of the reaction can be regulated by diluting the reaction system with an organic solvent that does not directly participate in the reaction. The same solvents as those mentioned above are suggested as the organic solvents used in such a case.

There are no limitations concerning the order of operations used in the second preparation process of the present invention, but for excellent reaction heat control, productivity, and reaction selectivity, it is preferable to use a process in which, after mixing component (B), component (G), and component (D), component (F) is added while heating or cooling the system as needed, and component (E) is further added after having reacted the above components to a certain extent. In the preparation process of the present invention, the progress of the reaction is tracked by gas chromatography etc., and, upon confirmation that a state of equilibrium has been achieved to a substantial degree, the acid is neutralized with a base. Furthermore, if necessary, the target silicone compounds can be obtained by removing the acids and salts from the reaction system by washing etc. and then using distillation or other conventional publicly known methods. The same compounds as those mentioned above are suggested as the bases used in the neutralization reaction. Although the temperature of the reaction varies depending on the combination of component (F) and component (B) and cannot be given for all possible cases, in general, it is preferred that the temperature should be in the range of from 0 to 80° C., and, especially, in the range of from 20 to 70° C. This is due to the tendency of the reaction to slow down when the reaction temperature is below this range, and, on the other hand, to the homocondensation of component (F) and the random re-arrangement of siloxane bonds in the resultant silicone compounds when it exceeds the range. In particular, when component (F) and component (B) have silicon-bonded hydrogen atoms, the reaction is preferably conducted at a temperature of from 0 to 80° C. because otherwise there is a tendency to bring about side reactions, such as the dehydration condensation with hydroxyl groups contained in the reaction system.

Examples of compounds suggested as the silicone compounds that can be obtained by using the processes of the present invention include, for instance, tetrakis(dimethylsiloxy)silane, tetrakis(dimethylvinylsiloxy)silane, 3-methacryloxypropyltris(trimethylsiloxy)silane, 3-methacryloxypropyltris(dimethylsiloxy)silane, vinyltris(trimethylsiloxy)silane, methyltris(dimethylsiloxy)silane, and siloxane compounds formed by substituting dimethylsiloxy, dimethylvinylsiloxy, or trimethylsiloxy groups for the alkoxy groups of the alkoxy-containing siloxane compounds suggested as examples of component (A).

In the above-described preparation processes of the present invention the alcohol and water formed as by-products during the reaction are eliminated by the carboxylic anhydride of (E), thereby suppressing the formation of silanol groups via the hydrolysis of alkoxy, aryloxy, and acyloxy groups, and, as result, permitting synthesis of the target silicone compounds in high purity. In addition, because the reaction system does not separate into two layers and remains homogeneous until the end of the reaction, the reactivity is increased such that the target silicone compounds are obtained within a shorter reaction time than in prior-art preparation techniques.

Such silicone compounds are useful as intermediates for various silicone polymers, as resin modifiers, and as additives or curing agents used in curable silicone compositions.

Hereinbelow, the present invention is explained in detail by referring to examples.

EXAMPLE 1

296 g (2.21 mol) 1,1,3,3-tetramethyldisiloxane, 165.7 g (2.76 mol) acetic acid, and 0.39 g trifluoromethanesulfonic acid were placed in a nitrogen-purged four-neck flask equipped with a stirrer and 140 g (0.92 mol) tetramethoxysilane was added thereto in a dropwise fashion over a period of 30 min while stirring the mixture at a temperature of 45° C. During the dropwise addition, the temperature of the reaction mixture was maintained at 45° C. by cooling or by other means, if necessary. Upon termination of the dropwise addition, the mixture was stirred for 30 min at 45° C. whereupon 187.7 g (1.84 mol) acetic anhydride was added thereto in a dropwise fashion. By periodically monitoring the progress of the reaction by gas chromatography (hereinafter called "GLC"), it was determined that the reaction was completed 30 min after the termination of the dropwise addition of the acetic anhydride. Upon completion of the reaction, the reaction solution was a transparent, homogenous system. Subsequently, the reaction was terminated by adding calcium carbonate and the target substance was obtained by removing low-boiling components and filtering off inorganic salts. The main product among the thus obtained reaction products was a silicone compound represented by the formula:

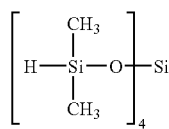

Its yield obtained by isolation at that point was 95.0% and the purity of the silicone compound was 96.0%. In addition, the by-product was a mixture of 1.8% of a partial condensate represented by the formula:

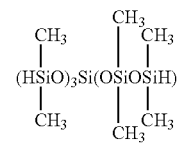

and 2.2% of a dimer represented by the formula:

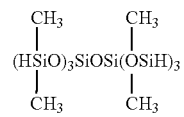

In addition, unreacted material represented by the formula:

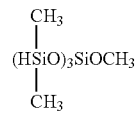

had been almost completely eliminated (with less than 0.5% left).

EXAMPLE 2

29.8 g (160 mmol) 1,3-divinyl-1,1,3,3-tetramethyldisiloxane, 15.6 g (260 mmol) acetic acid, and 0.03 g trifluoromethanesulfonic acid were placed in a nitrogen-purged four-neck flask equipped with a stirrer and 10 g (66 mmol) tetramethoxysilane was added thereto in a dropwise fashion over a period of 5 min while stirring the mixture at a temperature of 45° C. During the dropwise addition, the temperature of the reaction mixture was maintained at 45° C. by cooling or by other means, if necessary. Upon termination of the dropwise addition, the mixture was stirred for 30 min at 45° C., whereupon 13.3 g (130 mmol) acetic anhydride was added thereto in a dropwise fashion. By periodically monitoring the progress of the reaction by GLC, it was determined that the reaction was completed within approximately 3 hours after the termination of the dropwise addition of the acetic anhydride. Subsequently, the reaction was terminated by adding calcium carbonate and the target substance was obtained by removing low-boiling components and filtering off inorganic salts. The main product among the resultant reaction products was a silicone compound represented by the formula:

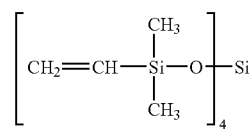

Its yield obtained by isolation at that point was 90.0% and the purity of the silicone compound was 93.1%. In addition, the by-product consisted of a mixture of 1.9% of unreacted material represented by the formula:

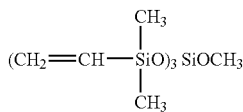

0.6% of a partial condensate represented by the formula:

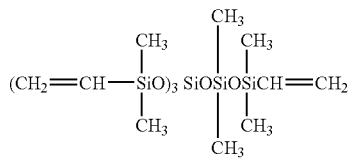

and 4.4% of a diner represented by the formula:

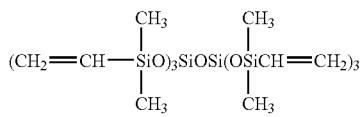

EXAMPLE 3

547 g (1.5 mol) hexamethyldisiloxane, 270 g (4.5 mol) acetic acid, and 0.35 g trifluoromethanesulfonic acid were placed in a nitrogen-purged four-neck flask equipped with a stirrer and 373 g (1.50 mol) methacryloxypropyltrimethoxysilane was added thereto in a dropwise fashion over a period of 50 min while stirring the mixture at a temperature of 45° C. During the dropwise addition, the temperature of the reaction mixture was maintained at 45° C. by cooling or by other means, if necessary. Upon termination of the dropwise addition, the mixture was stirred for 60 min at 45° C., whereupon 230 g (2.25 mol) acetic anhydride was added thereto in a dropwise fashion. By periodically monitoring the progress of the reaction by GLC, it was determined that the reaction was completed within approximately 15 min after the termination of the dropwise addition of the acetic anhydride. Subsequently, the reaction was terminated by adding calcium carbonate and the target substance was obtained by removing low-boiling components and filtering off inorganic salts. The main product among the resultant reaction products was a silicone compound represented by the formula:

$$\left[ CH_3 - \underset{\underset{CH_3}{|}}{\overset{\overset{CH_3}{|}}{Si}} - O \right]_3 Si - C_3H_6OCC = CH_2 \atop \underset{O}{\parallel}$$

The yield of the silicone compound was 97.2% and its purity was 98.7%. In addition, the by-product consisted of 1.3% of a diner represented by the formula:

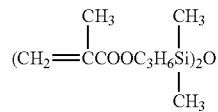

In addition, unreacted material represented by the formula:

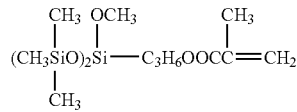

had been almost completely eliminated (with less than 0.5% left).

EXAMPLE 4

321 g (1.98 mol) hexamethyldisiloxane, 159 g (2.64 mol) acetic acid, and 0.20 g trifluoromethanesulfonic acid were placed in a nitrogen-purged four-neck flask equipped with a stirrer and 175 g (1.50 mol) 3-chloropropyltrimethoxysilane was added thereto in a dropwise fashion over a period of 40 min while stirring the mixture at a temperature of 45° C. During the dropwise addition, the temperature of the reaction mixture was maintained at 45° C. by cooling or by other means, if necessary. Upon termination of the dropwise addition, the mixture was stirred for 60 min at 45° C., whereupon 135 g (1.32 mol) acetic anhydride was added thereto in a dropwise fashion. By periodically monitoring the progress of the reaction by GLC, it was determined that the reaction was completed within approximately 60 min after the termination of the dropwise addition of the acetic anhydride. Subsequently, the reaction was terminated by adding calcium carbonate and the target substance was obtained by removing low-boiling components, filtering off inorganic salts, and then conducting distillation under reduced pressure. The main product among the resultant reaction products was a silicone compound represented by the formula:

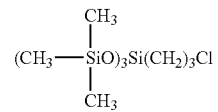

The yield of the silicone compound was 92.4%, and its purity 98.7%. In addition, the by-product consisted of 1.3% of a diner represented by the formula:

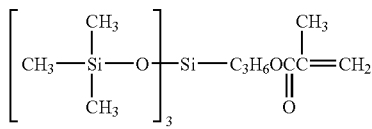

Also, unreacted material represented by the formula:

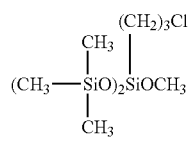

had been almost completely eliminated (with less than 0.5% left).

COMPARATIVE EXAMPLE 1

22.6 g (121 mmol) 1,3-divinyltetramethyldisiloxane, 7.3 g (121 mmol) acetic acid, 0.015 g trifluoromethanesulfonic acid, and 1 g toluene, which was used as the internal standard for GLC, were placed in a nitrogen-purged four-neck flask equipped with a stirrer and 8.4 g (55 mmol) tetramethoxysilane was added thereto in a dropwise fashion over a period of 50 min while stirring the mixture at room temperature. After reacting the components for 7 hours at 55° C., 0.04 g hexamethyldisilazane was added to the mixture and the reaction was terminated. At this point, the reaction solution had separated into an oil layer and a water layer. The main product among the resultant compounds was a silicone compound represented by the formula:

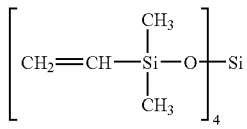

Its yield was 70% (corrected yield obtained by comparison with the standard). In addition, the by-product consisted of a mixture of unreacted material represented by the formula:

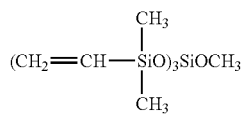

and a dimer represented by the formula:

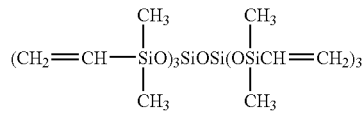

EXAMPLE 5

30.8 g (190 mmol) hexamethyldisiloxane, 9.92 g (3 1.0 mmol) methanol, and 0.020 g trifluoromethanesulfonic acid were placed in a nitrogen-purged four-neck flask equipped with a stirrer and 20 g (86.0 mmol) vinyltriacetoxysilane was added thereto in a dropwise fashion over a period of 40 min while stirring the mixture at a temperature of 45° C.

During the dropwise addition, the temperature of the reaction mixture was maintained at 45° C. by cooling or by other means, if necessary. Upon termination of the dropwise addition, the mixture was stirred for 30 min at 45° C., whereupon 13.3 g (130 mmol) acetic anhydride was added thereto in a dropwise fashion. By periodically monitoring the progress of the reaction by GLC, it was determined that the reaction was completed within approximately 40 min after the termination of the dropwise addition of the acetic anhydride. Subsequently, the reaction was terminated by adding calcium carbonate and the target substance was obtained by removing low-boiling components, filtering off inorganic salts, and conducting distillation under reduced pressure. The main product among the resultant reaction products was a silicone compound represented by the formula:

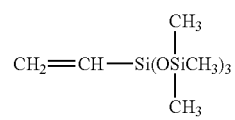

The yield obtained by isolation of the silicone compound was 95.1 %, and its purity 94.5%. In addition, the by-product consisted of 5.5% of a dimer represented by the formula:

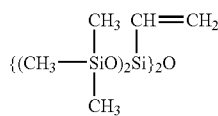

Also, unreacted material represented by the formula:

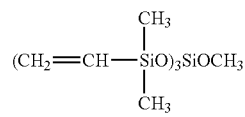

had been almost completely eliminated (with less than 0.5% left).

COMPARATIVE EXAMPLE 2

15.7 g (97.0 mmol) hexamethyldisiloxane, 4.5 g (140 mmol) methanol, and 0.020 g trifluoromethanesulfonic acid were placed in a nitrogen-purged four-neck flask equipped with a stirrer and 10 g (43.0 mmol) vinyltriacetoxysilane was added thereto in a dropwise fashion over a period of 15 min while stirring the mixture at a temperature of 45° C. During the dropwise addition, the temperature of the reaction mixture was maintained at 45° C. by cooling or by other means, if necessary. By periodically monitoring the progress of the reaction by GLC, it was determined that the reaction was completed within approximately 210 min after the termination of the dropwise addition of the acetoxysilane. Next, the reaction mixture was washed with water several times and extracted with hexane, whereupon the target substance was obtained by removing low-boiling components. The main product among the resultant reaction products was a silicone compound represented by the formula:

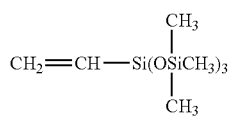

The yield obtained by isolation of the silicone compound was 85.0% and its purity was 88.9%. In addition, the by-product consisted of a mixture of 1.38% of unreacted material represented by the formula:

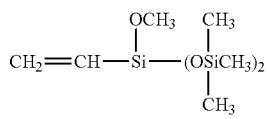

7.97% of a dimer represented by the formula:

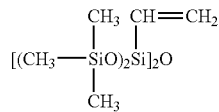

and 1.75% of silanol bodies represented by the formula:

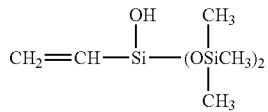

What is claimed is:

1. A process for preparing a silicone compound, the process comprising reacting (A) a silicon compound having silicon-bonded hydrolyzable groups selected from the group consisting of (i) alkoxy groups and (ii) silicon-bonded aryloxy groups and (B) a disiloxane compound having the formula:

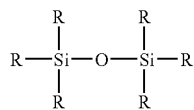

wherein R is an unsubstituted or substituted monovalent hydrocarbon group or a hydrogen atom, in the presence of (C) a carboxylic acid, (D) an acid catalyst, and (E) a carboxylic anhydride.

2. The process according to claim 1, wherein the mole ratio of component (B) to the hydrolyzable groups of component (A) is from 0.5 to 1.0.

3. The process according to claim 1, wherein the acid catalyst is selected from the group consisting of hydrochloric acid, sulfuric acid, and a perfluoroalkanesulfonic acid.

4. The process according to claim 1, wherein the carboxylic anhydride is selected from the group consisting of acetic anhydride and propionic anhydride.

5. The process according to claim 1, wherein the mole ratio of component (E) to component (C) is from 0.5 to 1.0.

6. The process according to claim 1, wherein component (E) is added while component (A) and component (B) are reacting in the presence of component (C) and component (D).

7. A process for preparing a silicone compound, the process comprising reacting (F) a silicon compound having silicon-bonded acyloxy groups and (B) a disiloxane compound having the formula:

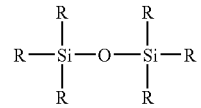

wherein R is an unsubstituted or substituted monovalent hydrocarbon group or a hydrogen atom, in the presence of (D) an acid catalyst, (E) a carboxylic anhydride, and (G) an alcohol.

8. The process according to claim 7, wherein the mole ratio of component (B) to acyloxy groups of component (F) is from 0.5 to 1.0.

9. The process according to claim 7, wherein the acid catalyst is selected from the group consisting of hydrochloric acid, sulfuric acid, and a perfluoroalkanesulfonic acid.

10. The process according to claim 7, wherein the carboxylic anhydride is selected from the group consisting of acetic anhydride and propionic anhydride.

11. The process according to claim 7, wherein the mole ratio of component (E) to component (G) is from 0.5 to 1.0.

12. The process according to claim 7, wherein component (E) is added while component (F) and component (B) are reacting in the presence of component (G) and component (D).

* * * * *